United States Patent
Dubernard (10) Patent No.: US 9,861,460 B2
(45) Date of Patent: Jan. 9, 2018

(54) SUBURETHRAL HAMMOCK

(75) Inventor: Pierre Dubernard, Lyons (FR)

(73) Assignee: COUSIN BIOTECH, Wervicq-sud (FR)

( * ) Notice: Subject to any disclaimer, the term of this patent is extended or adjusted under 35 U.S.C. 154(b) by 1575 days.

(21) Appl. No.: 12/375,723

(22) PCT Filed: Jul. 31, 2007

(86) PCT No.: PCT/FR2007/001321
§ 371 (c)(1),
(2), (4) Date: Nov. 20, 2009

(87) PCT Pub. No.: WO2008/015338
PCT Pub. Date: Feb. 7, 2008

(65) Prior Publication Data
US 2010/0130814 A1 May 27, 2010

Related U.S. Application Data (60) Provisional application No. 61/821,153, filed on Aug. 2, 2006.

(51) Int. Cl.
| | | |
|---|---|---|
| A61F 2/02 | (2006.01) |
| A61F 2/00 | (2006.01) |
| A61B 17/06 | (2006.01) |
| A61B 17/34 | (2006.01) |
| A61B 17/00 | (2006.01) |
| A61F 2/30 | (2006.01) |

(52) U.S. Cl.
CPC ...... *A61F 2/0045* (2013.01); *A61B 17/06109* (2013.01); *A61B 17/3468* (2013.01); *A61B 2017/00805* (2013.01); *A61F 2/0063* (2013.01); *A61F 2002/30537* (2013.01); *A61F 2250/0004* (2013.01); *Y10S 128/25* (2013.01)

(58) Field of Classification Search
CPC ........... A61F 2/0045; A61F 2250/0004; A61B 2017/00805
USPC ........ 600/29, 30, 37; 128/897–899; 606/151
See application file for complete search history.

(56) References Cited

U.S. PATENT DOCUMENTS

| | | | | |
|---|---|---|---|---|
| 5,013,292 | A * | 5/1991 | Lemay | 600/30 |
| 5,562,689 | A * | 10/1996 | Green et al. | 606/151 |
| 6,010,447 | A * | 1/2000 | Kardjian | 600/29 |
| 6,042,534 | A * | 3/2000 | Gellman et al. | 600/30 |
| 6,042,536 | A * | 3/2000 | Tihon et al. | 600/37 |
| 6,068,591 | A * | 5/2000 | Bruckner et al. | 600/30 |
| 6,221,005 | B1 * | 4/2001 | Bruckner et al. | 600/30 |
| 7,588,598 | B2 * | 9/2009 | Delorme et al. | 623/11.11 |
| 8,025,619 | B2 * | 9/2011 | Gellman | 600/30 |
| 2003/0220538 | A1 * | 11/2003 | Jacquetin | 600/37 |

(Continued)

FOREIGN PATENT DOCUMENTS

WO WO 0145589 A1 * 6/2001

*Primary Examiner* — Charles A Marmor, II
*Assistant Examiner* — Shannon McBridge
(74) *Attorney, Agent, or Firm* — MH2 Technology Law Group, LLP (57) ABSTRACT

An implantable prosthesis for the treatment of incontinence is disclosed having a support element designed to be placed under the urethra in order to prevent the urethra from moving away in the direction of the lower pelvis and to prevent any uncontrolled intra-urethral flow. A surgical instrument used to implant the prosthesis is also disclosed as is a method of implantation.

17 Claims, 6 Drawing Sheets

(56) References Cited

U.S. PATENT DOCUMENTS

2004/0087970 A1\* 5/2004 Chu et al. .................... 606/119
2004/0215054 A1\* 10/2004 Siegel et al. .................. 600/31
2005/0283040 A1\* 12/2005 Greenhalgh .................. 600/30
2006/0205995 A1\* 9/2006 Browning ..................... 600/29

\* cited by examiner

SUBURETHRAL HAMMOCK

CROSS REFERENCE RELATED APPLICATIONS

This application is a national phase of PCT/FR2007/001321 filed Jul. 31, 2007, which claims priority to U.S. Provisional Ser. No. 60/821,153 filed Aug. 2, 2006, which is entirely incorporated herein by reference.

TECHNICAL FIELD

This invention relates to the general field of medical devices used for the treatment of incontinence, notably urinary incontinence.

This invention relates in particular to an implantable prosthesis for the treatment of incontinence, comprising a retaining means having a support element designed to be placed under the urethra in order to prevent the latter moving away in the direction of the lower pelvis, and to prevent any uncontrolled intra-urethral flow.

This invention also relates to a surgical instrument used to implant a prosthesis to treat incontinence.

This invention also relates to a surgical method to treat incontinence.

PRIOR ART

It is common to use surgically implanted medical devices in order to treat incontinence, notably urinary incontinence.

Incontinence of this nature can result from an alteration of the natural sphincterian functions of the patient; for example, with males as a result of a prostatectomy. With females, another form of incontinence, known as "stress" incontinence can also result from a looseness of the pelvic tissues leading to a hyper-mobility of the urethra.

The type of medical device implanted depends on the nature and severity of the incontinence, as well as on the patient's sex.

Thus, in the case of mild to moderate incontinence for females, such as stress incontinence, it is common to implant a tension-free vaginal tape (TVT) positioned transversely under the urethra, in the tissues, without any significant tension.

In the case of males suffering from mild to moderate incontinence, it is common to implant a textile plate underneath the urethra, stretched by fixing each of its extremities to one of the branches of the ischiopubic ramus.

In the case of more severe incontinence, it is generally necessary to use an artificial sphincter, which usually contains a sleeve design to surround the urethra, containing, on its inside face, an inflatable annular pocket which, when inflated, leads to the occlusion of the urethra via constriction.

Although delivering satisfactory results from a therapeutic point of view, such devices from the prior art have a number of non-negligible drawbacks.

Specifically, it is sometimes noticed, following implantation of a tape such as TVT, that it is insufficiently efficient to resolve the incontinence problem.

In this case, it is necessary to carry out a second surgical intervention to replace the aforementioned tape with an artificial sphincter, which exposes the patient to a new traumatism and new complications.

Moreover, currently used artificial sphincters are relatively expensive, and implanting such artificial sphincters is a relatively complex surgical intervention.

As regards textiles plates, they are frequently attached to the pubic bone by means of anchoring elements, such as screws, which increases the traumatism suffered by the patient, and can be a source of complications.

STATEMENT OF INVENTION

It is therefore the object of the invention to propose a new implantable prosthesis to treat incontinence without the drawbacks detailed above, and which can be used to efficiently treat various degrees of incontinence, whilst being particularly easy to implant.

It is another object of the invention to propose a new prosthesis which would be particularly atraumatic and would substantially reduce the discomfort caused to the patient, as well as the risk of post-operation complications.

It is another object of the invention to propose a new prosthesis of particularly simple design and relatively inexpensive.

It is another object of the invention to propose a new prosthesis with a good level of mechanical stability and highly resistant in time.

It is another object of the invention to propose a new prosthesis particularly suited to treat male urinary incontinence.

It is another object of the invention to propose a new prosthesis whose implementation can be adapted to the patient's anatomy.

It is also an object of the invention to propose a new prosthesis for the combined treatment of female urinary incontinence and cervico-cystoptosis.

It is also an object of the invention to propose a new ancillary enabling a quick, easy, and particularly safe implantation of a prosthesis to treat incontinence according to the invention.

It is also an object of the invention to propose a new method for the surgical treatment of incontinence, said method particularly safe and efficient.

It is also an object of the invention to propose a new method for the surgical treatment of incontinence, said method being insignificantly traumatizing for the patient.

It is another object of the invention to propose a new method for the surgical treatment of incontinence, said method polyvalent and adaptable to each patient, regardless of sex, age or corpulence.

It is also an object of the invention to propose a new surgical method particularly suited to treating male urinary incontinence.

Lastly, it is also an object of the invention to propose a new surgical method particularly suited to treating female urinary incontinence.

The objects of the invention are reached using an implantable prosthesis comprising a retaining means having a support element designed to be placed under the urethra in order to prevent the latter from moving away in the direction of the lower pelvis, and to prevent any uncontrolled intraurethral flow, said prosthesis characterized in that it comprises:

An atraumatic suspension means provided with at least one bearing element, arranged so as to overlap part of the pubic bone, and to rest on the latter, and at least one sling, connecting said bearing element to the retaining means, said sling being designed to hold the support element at a substantially constant distance from the pubic bone, called the retaining distance, A means for reversibly adjusting the retaining distance, thus making it possible to reversibly vary said retaining distance.

The objects of the invention are also reached by means of a surgical instrument used to implant a prosthesis to treat incontinence, comprising a retaining means having a support element, an atraumatic suspension means, provided with at least one bearing element arranged so as to overlap part of the pubic bone and to rest on the latter, and at least one sling connecting the bearing element to the retaining means in order to hold the support element at a substantially constant retaining distance from the pubic bone, said surgical instrument fitted with an introduction element designed to be inserted in the tissues situated in the retropubic space in order to therein open a passageway intended for one or the other of the slings, said introduction element comprising at least a proximal portion arranged to penetrate the tissues, a distal portion connected to a gripping means, and an intermediate section connecting the proximal portion to the distal portion, and having an exterior lateral surface in contact with the tissues traversed, said surgical instrument characterized in that the intermediate section comprises at least a lateral orifice connecting its exterior lateral surface to a collecting duct so as to be able to collect the liquid contained in the bladder when the introduction element accidentally perforates the latter.

Lastly, the objects of the invention are also reached by means of a surgical method to treat incontinence, comprising an engagement step (a) during which is implanted, under the urethra, a retaining means having a support element, designed to prevent the urethra from moving away in the direction of the lower pelvis, and to prevent any uncontrolled intra-urethral flow, said surgical method characterized in that it comprises an atraumatic bone suspension step (b) during which the retaining means is suspended to the pubic bone by means of an atraumatic suspension means in such a way that the support element is maintained at a substantially constant distance from the pubic bone, and more particularly from the symphysis pubica, called the retaining distance ($d_0$) as well as a suspension tension adjustment step (c) during which the medical practitioner adjusts the retaining distance in vivo in order to regulate the suspension stress exerted by the support element on the urethra.

BRIEF DESCRIPTION OF THE FIGURES

Other advantages and objects of the invention will appear in greater detail on reading of the description which follows, and with the help of the appended drawings which are supplied purely for explanation and are not limitative, in which.

DETAILED DESCRIPTION

This invention relates to an implantable prosthesis 1 used to treat incontinence, and more preferably, urinary incontinence. Advantageously, the prosthesis 1 of the invention can be adapted to treat various types and degrees of urinary incontinence, both male and female.

Thus, the said prosthesis 1 can be adapted to treat light, moderate or severe incontinence in males, caused by sphincterian insufficiency, by replacing the natural sphincterian function.

The prosthesis 1 can also be adapted to treat effort incontinence in females caused by a hyper-mobility of the urethra and the urinary bladder neck. In particular, the said prosthesis 1 can be advantageously used in females when other operating techniques have failed.

The prosthesis 1 of the invention comprises a retaining means designed to be placed under the urethra U in order to prevent the latter moving away in the direction of the lower pelvis, and to prevent any uncontrolled intra-urethral flow.

According to the invention, the support element 3 can either be in direct contact with the bottom part of the urethra; i.e. with that part of the urethra substantially oriented towards the patient's lower members, or said support element 3 can be in indirect contact with the underlying tissues joining said urethra.

The configuration of the contact can depend on the patient's sex; for females, the support element 3 will be preferably applied directly against the urethra, whereas for males, the said support element 3 will be preferably placed against the bulbospongious muscle MBC.

Naturally, the surface condition and the surface area of the support element 3 intended to be actually positioned against the tissues (urethra or bulbospongious muscle) should also be chosen to give the said support element 3 a substantially atraumatic nature.

According to an important characteristic of the invention, the prosthesis 1 comprises an atraumatic suspension means 4 with at least one bearing element 5, said bearing element arranged so as to overlap part of the pubic bone OP and to rest on the latter, and at least one sling 6, 7 connecting said bearing element 5 to the suspension means 2, said sling 6, 7 being designed to hold the support element 3 at a substantially constant distance from the pubic bone OP, and particularly from the symphysis pubica SP, called the retaining distance $d_0$. In other terms, the atraumatic suspension means 4 is arranged to mechanically link the retaining means 2, and more specifically its' support element 3 to the pubic bone OP so that said support element 3 prevents possible displacement of the urethra in moving away from the pubic bone, and more particularly from the symphysis pubica SP. The support element 3 thus forms an "anti-fall" stop which substantially retains the urethra at a predetermined "maximum" retaining distance $d_0$ from the said symphysis pubica by substantially resisting the effects of gravity.

Thus, the support element 3 is liable to exert a holding force or "suspension stress" F which prevents the urethra U from moving away from the symphysis pubica and, more precisely, from sinking down towards the bottom of the pelvis.

Depending on the patient's age and corpulence, the retaining distance $d_0$ will be preferably between approximately 5 cm and 20 cm, and preferably between 8 cm and 15 cm.

By "atraumatic suspension" it is meant that the suspension means 4, and more particularly, the bearing element 5 is designed so as not to damage the tissues on which it is resting and in particular to respect the integrity of the pubic bone.

More particularly, the suspension means 5 according to the invention will not have any anchoring elements that are prominent, cutting, perforating or abrasive such as tips, lugs or screws, liable to perforate, lacerate or crack the pubic bone, at the surface or inside said pubic bone, and/or nearby tissues.

According to another characteristic of the invention, the prostheses 1 comprises a means 20 for reversibly adjusting the retaining distance $d_0$ thus making it possible to vary said retaining distance $d_0$.

By "reversibly" is meant that the means of adjustment allows for increasing as well as decreasing the retaining distance $d_0$, said means being however "fixed" in the sense that the retaining distance $d_0$ is durably maintained once the prosthesis is implanted. Thus, the means 20 of adjustment is designed to substantially maintain said retaining distance constant, in normal operation, in such a way that the latter is not, for example, spontaneously changeable in a dynamic manner when subjected to forces from the patient's various organs.

However, the said retaining distance can be advantageously once again modified without any difficulty in the course of a voluntary therapeutic action undertaken by the doctor, for example, in the course of a minor subsequent surgical intervention whereby the surgeon accesses the means of adjustment by a simple and short suprapubic incision, without having to undertake a major dissection to completely reveal the urethra.

The said means of adjustment 20 advantageously permits the medical practitioner to freely choose, notably when implanting the prosthesis 1, the distance at which he positions the end stop comprising the support element 3, and to adjust the retaining distance according to the patient's specific anatomy. In this way, the same standard prosthesis 1 model can be used to treat several patients.

Moreover, and in a particularly advantageous manner, the means of adjustment 20 can be used, depending on the tightening effect obtained by the distance, more or less near, between the retaining means 2 and the symphysis pubica SP, to adjust the intensity of the suspension stress F.

More precisely, the more we try to reduce the distance $d_0$, the more traction is generated in the slings 6, 7, and the more we tend to compress the urethra U against the overhanging tissues, by exerting on the said urethra, a force from bottom to top, and substantially oriented in the direction of an imaginary straight line between the base of the urethra U in contact with the support element 3 and the symphysis pubica SP.

Thus, it is possible to opt for an "active" suspension whereby the prosthesis 1 permanently exerts a non-null suspension stress F on the urethra. In particular, such a solution could be used to treat urinary incontinence in males.

By contrast, it is possible to obtain, with the same means of adjustment 20, a "passive" suspension; i.e., a loose holding, of the urethra by adjusting the retaining distance $d_0$ so that it substantially corresponds to the natural anatomical distance when resting, and so that the suspension stress F exerted by the prosthesis 1 be substantially null by default.

Figure 10:
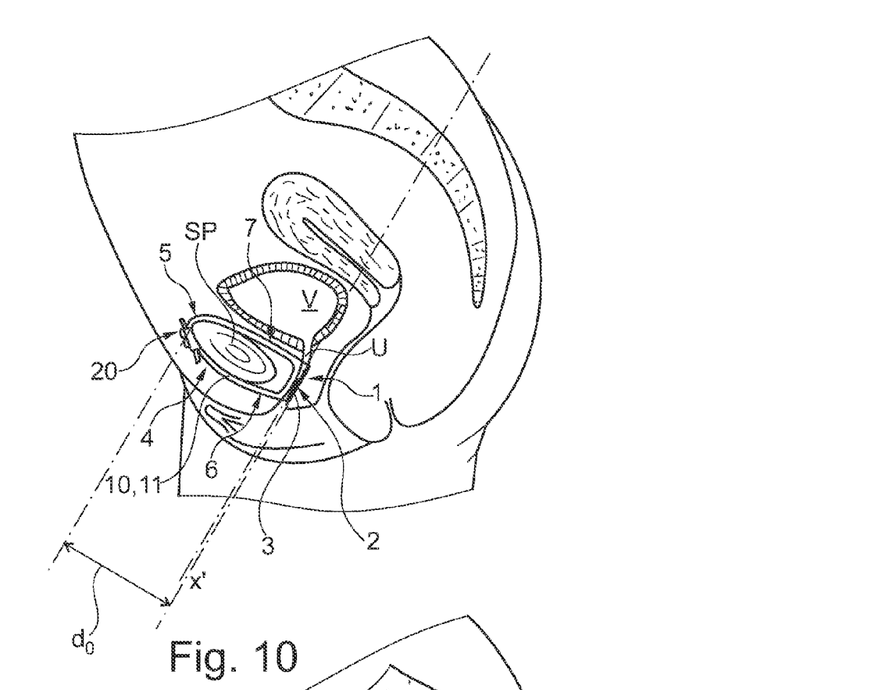
FIG. 10 illustrates, from a simplified side sectional view, the implementation, in a female, of an embodiment of the prosthesis according to the invention.

In other terms, it is possible to use the means of adjustment 20 to position the support element 3 substantially in contact against the urethra, without stresses, or "without tension", as illustrated in FIG. 10, so that said support element 3 form a sort of barrier, and that a stress emerges only when the urethra tries to "flee" the symphysis pubica by pulling on the slings. Such a solution is particularly appropriate for treating stress incontinence in females, notably because of the risk of eroding the highly delicate tissues of the urethra.

Thus, the support element 3 according to the invention can be more or less compressive and its implementation adapted depending on whether the purpose is to simply maintain, without residual compression, the urethral roof in a functional configuration (as is the case with females) or whether the purpose is to exert and maintain a permanent residual compression of the urethra (as is the case with males).

According to an embodiment (not shown), the suspension means 4 can be arranged to permit the suspension "in the manner of a transobturator" of the retaining means 2; i.e., the bearing element 5 is designed to be urged to be supported on an ischiopubic branch or on an iliopubic branch, and more particularly on the top side of one of the said branches.

With this embodiment, one or the other of the slings 6, 7 is preferably arranged to connect the retaining means 2 to the bearing element 5 by passing through the obturator foramen.

However, in a particularly preferential manner, the suspension means 4 comprises a peri-symphyseal suspension means designed to suspend the retaining means 2 to the symphysis pubica SP.

Such a suspension mode offers several advantages in terms of stability, functional efficacy and simplicity of suspension.

To simplify the description, it will therefore be considered for the remainder of this text that the prosthesis 1 is intended to be suspended to the symphysis pubica, without however this constituting a limitation to the invention.

Preferably, the suspension means 4 comprises at least one anterior sling 6 and one posterior sling arranged to connect the bearing element 5 to the retaining means 2 by passing, respectively, in front of, and behind, the symphysis pubica SP.

The bearing element 5 can therefore advantageously position itself around the pubic bone, so as to marry, at least partially, the contour of the latter, and more particularly, the top side of said contour.

In the sense of the invention, the bearing element 5 of the invention constitutes a mechanical support point, i.e., has a contact surface with the underlying tissues; a surface along which a force can be transmitted, said force used, in this case, to provide the suspension.

In this respect, it is remarkable that the pubic bone OP, and more particularly the symphysis pubica SP, offers a particularly rigid, resistant and stable point of suspension, which confers a good level of seating to the prosthesis 1.

Moreover, the suspension of the invention is advantageously a "free" suspension, i.e., the bearing element 5 is simply put down on the symphysis pubica, without having to be thereto anchored, for example by stitching, stapling or knotting.

Moreover, even though it is conceivable to engage the bearing element 5 above the symphysis pubica at a distance from the latter, thus compressing the tissues trapped between said bearing element 5 and the top surface of the symphysis pubica SP (such as muscular aponeurosis), it is nevertheless preferable that the bearing element 5 be in contact against the pubic bone, and rest directly on the top edge of the symphysis pubica which it overlaps.

Advantageously, such a system guarantees the lateral holding of the prosthesis 1, and more precisely the bearing element 5, by the pubic spine which acts as an end stop.

According to an embodiment not shown, the bearing element 5 can take the form of a sort of U-shaped saddle used to enclose the symphysis pubica.

It is remarkable that the peri-symphyseal suspension means of the invention provides the retaining means 2 with a mechanical fixing point substantially vertically in line the urethra U, thereby allowing for a "direct" suspension; i.e., one which, unlike the tapes or plates of the prior art, causes the direction of the suspension stress F to substantially coincide with the stressing direction of the elements comprising the suspension means 4.

Indeed, tapes or plates of the prior art are intended to be put down transversely under the pubis, and under the urethra in such a way that, to generate a resulting suspension stress, even a weak one, said tapes or plates need a significant transversal stressing which can traumatize the soft tissues or bone tissues into which their extremities are fixed.

This is why the preferential suspension means 4 according to the invention can be used advantageously to minimize the forces exerted on the said fixing tissues, since said means 4 converts almost all the stresses exerted on said fixing tissues into a useful suspension stress F.

Moreover, as will be detailed below, such a mode of symphyseal fixing advantageously makes for a holding that is more stable, encloses more of the urethra, improves the urinary continence of prosthesis 1, and is easier to implant than an artificial sphincter.

Figure 1:
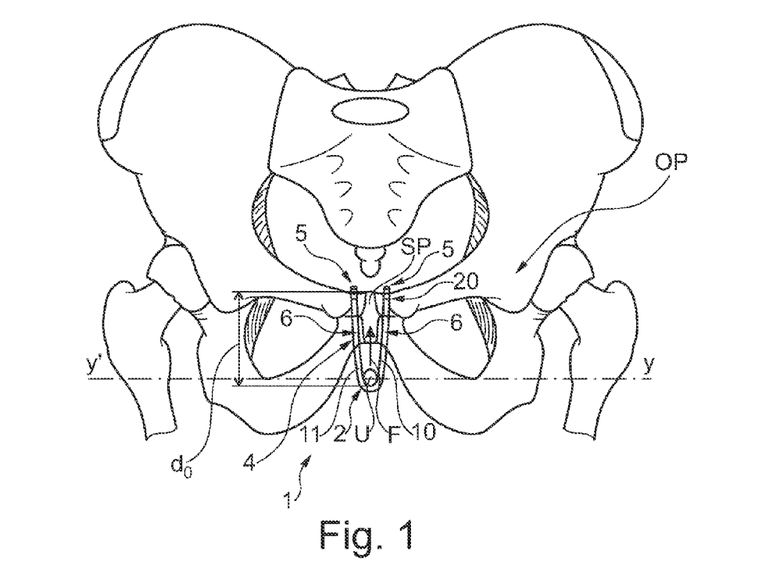
FIG. 1 illustrates, from an anterior front view, the implementation of an embodiment of the implantable prosthesis according to the invention.
Figure 3:
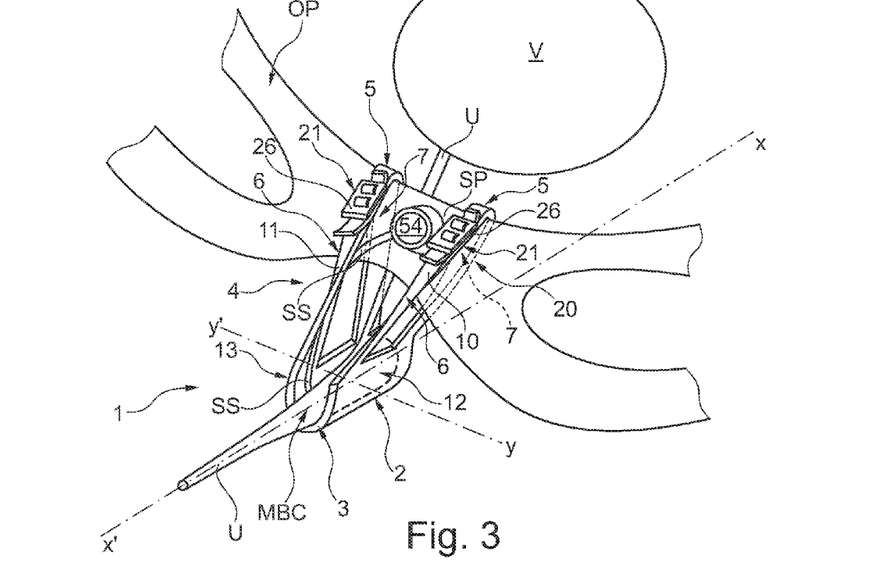
FIG. 3 illustrates, from a partial schematic perspective view, the implementation of an embodiment of the prosthesis corresponding to that of FIG. 2.

Preferably, as shown in FIGS. 1 and 3, the suspension means 4 comprises at least 2 suspension harnesses 10, 11 each of which has an anterior sling 6, a bearing element 5 and a posterior sling 7.

Naturally, the above-mentioned elements can be initially separate and then assembled using any nature of a mechanical joining means, or, on the contrary, the one and/or the other sling 6, 7 can form a single piece with the bearing element 5 and/or the retaining means 2.

By convention, the adjective "anterior" refers to an element in the area between the symphysis pubica and the anterior teguments of the patient, whereas the adjective "posterior" refers to a retropubic element located between the symphysis pubica and the pelvic cavity.

Thus, as shown in FIGS. 1 to 3 and 7, each suspension harness 10, 11 forms substantially an arch whose slings form the feet, and whose curved portion, which envelops, or "mounts" the top side of the symphysis pubica, forms the bearing element 5.

Figure 2:
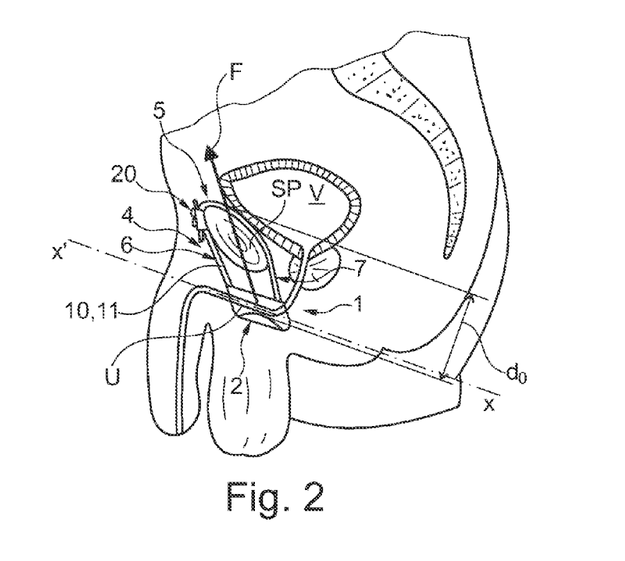
FIG. 2 illustrates, from a schematic side view, the implementation, in a male, of an embodiment of the prosthesis according to the invention.

As shown in figures in FIG. 2, 3 or 10, each harness thus advantageously forms, in cooperation with a part of the retaining means 2, a loop, preferably single, through which the symphysis pubica passes.

Preferably, the support element 3 and more globally, the suspension means 2, is divided into a left area 3G and a right area 3D located on along both sides of an imaginary center line (L) substantially parallel to the main extension direction (XX') of the urethra U when the prosthesis is implanted, and the suspension means 4 has a left harness 10 and a right harness 11, said left and right harnesses 10 and 11 respectively attached to the retaining means in the left area 3G and in the right area 3D.

Such an arrangement permits advantageously to balance and stabilize the suspension by enabling the medical practitioner to pass the left harness to the left of the urethra and the right harness to the right of the urethra.

Figure 4:
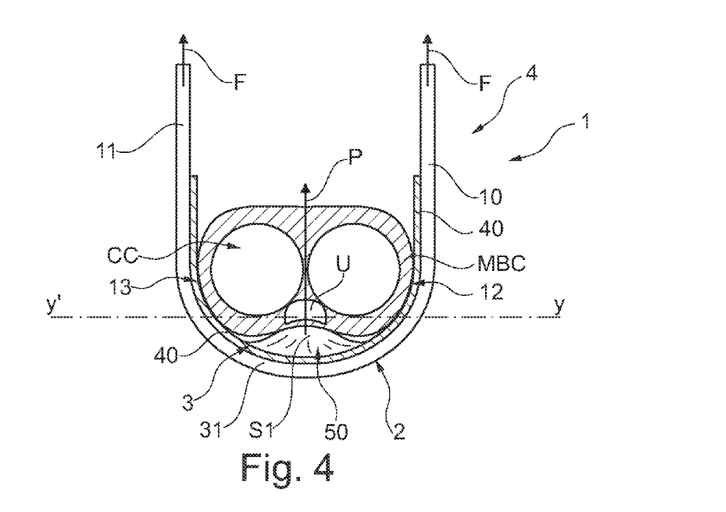
FIG. 4 illustrates, from a partial sectional front view, the operating principle, in a male, of an embodiment of the prosthesis according to the invention.

Moreover, the retaining means 2 preferably comprises, as shown in FIGS. 3 and 4, lateral holding elements 12, 13, and in this specific case, at least one left lateral holding element 12 and one right lateral holding element 13, designed to be placed on each side of the urethra U and prevent the lateral displacement of the latter.

In a particularly preferential manner, the lateral holding elements 12, 13 and the support element 3 consists of a single piece.

Such an embodiment permits advantageously firstly to substantially envelop the urethra inside a bearing structure forming a sort of hammock, or retention harness, intrinsically limiting the displacement of the urethra in the left-lateral, right-lateral, and lower-vertical directions, and secondly, to stabilize the retaining means 2 using two triangular structures formed by the slings of each of the harnesses 10, 11.

More globally, it is remarkable that the prosthesis 1 of the invention has preferably a globally symmetrical structure; i.e., that its' left portion correspond substantially to the image of its' right portion through a symmetrical plane which corresponds substantially to the sagittal plane of the patient.

A person skilled in the art will be naturally in a position to determine the suitable length of the harnesses 10, 11 according to the patient's age and corpulence.

For example, the total length of each of the said harnesses 10, 11 will preferably be between 10 cm and 50 cm approximately, and even more preferably between the 15 cm and 25 cm approximately.

Preferably, the harnesses, and more generally the suspension means 4, are designed to be sufficiently flexible to enable their implantation, and notably their inflexion above the symphysis, whilst having low extendability so as to substantially support, without longitudinal deformation, the traction stress providing the suspension of the retaining means 2 to the said symphysis.

Moreover, the said harnesses will be preferably non-adhesive.

Thus, one and/or the other of the harnesses 10, 11 could be formed on the basis of a band made from a polymer material, for example, polytetrafluoroethylene (PTFE)

One and/or the other of the harnesses 10, 11 could also be formed on the basis of a band made from a composite material comprising an implantable textile insert, such as polypropylene or polyester, and an elastomer coating or matrix, such as silicon.

It is also conceivable to carry out a surface treatment in order to make the textile anti-adhesive, for example by applying a fluoride gas plasma procedure, such as C2H2F4.

Preferably, the width of the said band will be substantially between 0.5 cm and 3 cm, and particularly preferably substantially equal to 1 cm, whilst its thickness will be preferably between 0.2 mm and 1 mm.

Advantageously, using bands enables the harness flats to position themselves substantially around the pubic bone, by taking on the form of the latter so as to distribute the suspension stresses over a relatively large surface. According to another embodiment (not shown), in particular when the suspension is done practically without tension, for example with females, the harnesses can be formed by thin cords, of a diameter, for example, between 1 mm and 3 mm.

Moreover, in order to facilitate the implantation of the prosthesis 1, one and/or the other of the harnesses is, before implantation, divided into a first strand 10A, 11A and a second strand 10B, 11B each of which has a captive extremity, attached to the retaining means 4, and a free extremity.

Thus, advantageously, each harness 10, 11 can be re-created in vivo by joining the free extremity of its first strand 10A, 11A with the free extremity of its second strand 10B, 11B, said first and second strands having being first put into the tissues on both sides of the symphysis pubica.

In particular, the first and second strands can substantially correspond to the anterior and posterior slings respectively.

Moreover, according to an embodiment not shown, it is entirely conceivable that one or both of the harnesses be formed by a single strand attached by one of its extremities to the retaining means 2, and whose free extremity can be bent back onto the said retaining means 2 after having been first passed around the symphysis.

Moreover, according to a preferential arrangement variation (not shown), the means 20 for adjusting the retaining distance will be substantially located in the proximity of the retaining means 2, at the base of the anterior sling 6, so as to be easily accessible and maneuverable by the surgeon.

Preferably, as is illustrated on FIG. 3, the means 20 for adjusting the retaining distance has an element 21 to adjust the length of one or the other of the slings 6, 7 and more precisely, one or the other of the harnesses 10, 11.

More particularly, the means of adjustment for reversibly adjusting the retaining distance $d_0$ permits both the extension as well as the shortening of said harnesses 10, 11.

Naturally, any discrete or continuous means of adjustment of the length of the harnesses is within the scope of the invention.

Thus, according to an embodiment, the means 20 for reversibly adjusting the retaining distance is designed to allow a discrete modification of the retaining distance $d_0$.

Figure 5:
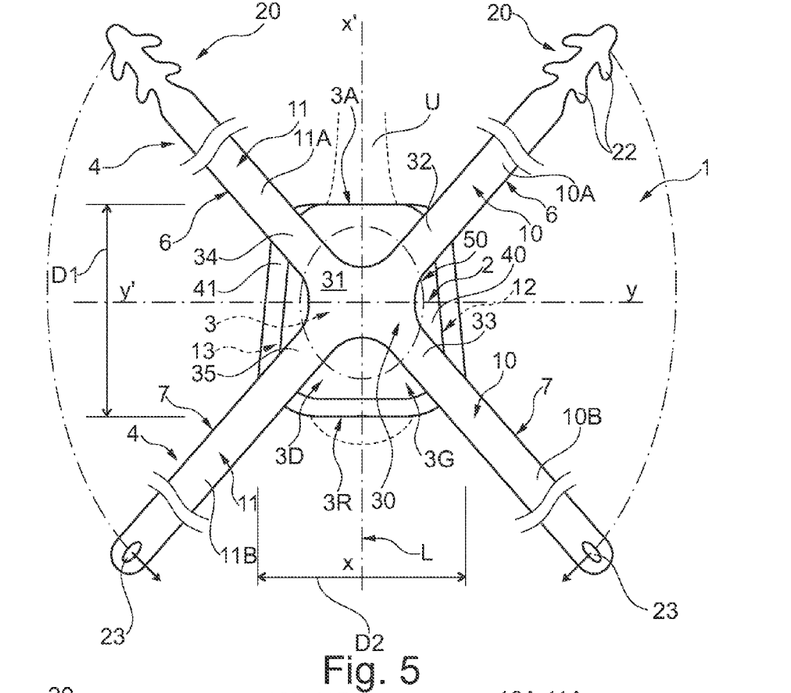
FIG. 5 illustrates, from a bottom view, an embodiment of the prosthesis according to the invention particularly suited to the treatment of male incontinence.
Figure 6A:
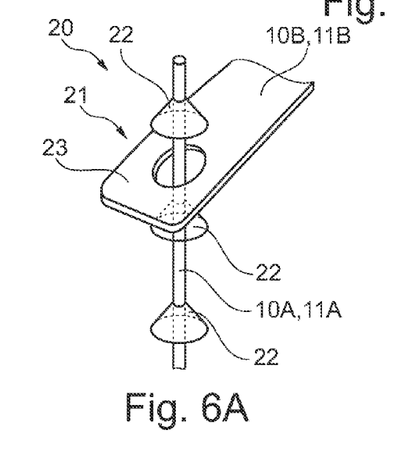
FIGS. 6A and 6B illustrate, respectively, from a partial perspective view and a sectional view, a first embodiment of the means for adjusting the retaining distance, liable to be used with an implantable prosthesis according to the invention.
Figure 6B:
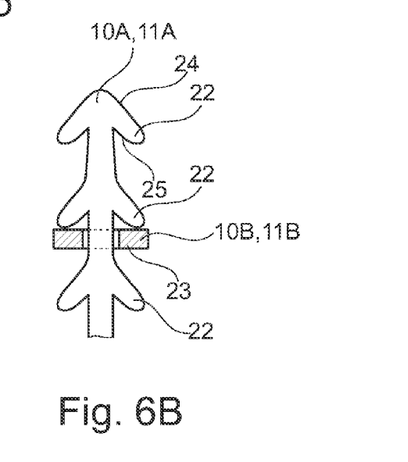
Figures 7, 8A:
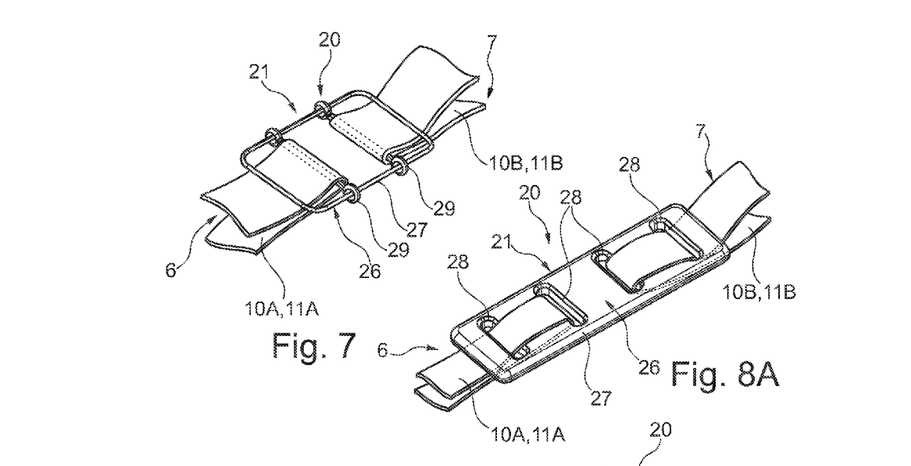
FIG. 7 illustrates, from a partial perspective view, a second embodiment of the means for adjusting the retaining distance, liable to be used with an implantable prosthesis according to the invention.
FIGS. 8A and 8B illustrate, from a partial perspective view and a longitudinal sectional view, a third embodiment of the means for adjusting the retaining distance, liable to be used with an implantable prosthesis according to the invention.

More particularly, as shown in FIGS. 5, 6A and 6B, the element 21 to adjust the length can include several "male" fixing elements 22 distributed along the first strand 10A, 11A as well as one or more matching "female" fixing elements 23 associated with the second strand 10B, 11B in such a way that the effective length of the corresponding harness 10, 11 can be adjusted, by a predetermined incremental step, according to the pair of fixing elements 22, 23 used.

As shown in FIGS. 5, 6A and 6B, the male fixing elements can be formed using full or hollow conic protuberance, or by anchors with one or more deformable branches, for example arranged by cutting the strand making up the harness.

The female fixing element, or elements, 23 can be formed by pull-through orifices, such as button hole orifices, whose lips may be deformable, and able to cooperate by clicking into the male fixing elements 22.

To this end, the male fixing elements 22 associated with the first strand, 11A comprising preferably a sloping introduction face 24 and an retaining face 25, with the passage of the first strand through the second strand 10B, 11B taking place by forcing the deformation of the protuberances and/or the orifice.

Figure 12:
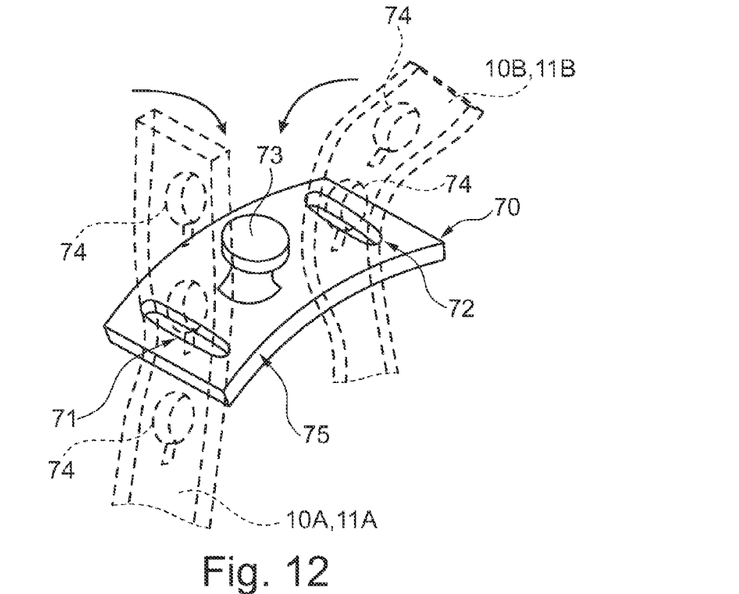
FIG. 12 illustrates, from a partial perspective view, a fourth embodiment of the means for adjusting the retaining distance, liable to be used with an implantable prosthesis according to the invention.

According to an embodiment shown in FIG. 12, it is possible to use a stop element 70 with one or several orifices 71, 72 drilled through the width of said element 70 to allow the passing of strands (shown as dotted lines in FIG. 12), and having a central protuberance 73 on its top side, said protuberance forming an anchoring button with which the button hole openings 74 drilled in the strands cooperate, when said strands are pushed back against the stop element 70 in the direction shown by the arrows. In particular, the button hole openings can have the form of clefted circular recesses.

An arrangement of this nature has the advantage of being simple, inexpensive and compact.

If necessary, the stop element 70 can comprise a flexible and/or curving base 75 intended to rest on the top side of the symphysis pubica, and form a part of the bearing element 5.

Preferably, the means 20 for adjusting the retaining distance will be designed to enable continuous modification of the retaining distance $d_0$; i.e., will permit without restriction the free selection of said retaining distance from amongst all intermediate values in a predetermined range.

To this effect, the element 21 to adjust the length comprises, preferably, as shown in FIGS. 3, 7, 8A and 8B, a tightening loop 26 wrapped around a sling 6, 7, and arranged to allow a continuous adjustment of the length of said sling.

The said tightening loop which may be somewhat comparable with loops used on handbag straps or rucksack straps will comprise, for example, a frame 27, preferably rigid or semi-rigid, with fixed orifices 28 drilled into its width, or provided with sliding crossbars 29, the purpose of said frame being to hold the strands when folded on themselves, and to stop the latter by crushing.

Thus, the tightening loop 26 will act as a clasp permitting to join together, in pairs, the anterior strands 10A and posterior strands 10B of a given harness 10 in order to reconstitute the latter by giving it the desired length.

Preferably, the adjustment range given by the element 21 to adjust the length according to the invention, notably in the case of discrete adjustment means, is substantially included between 0.5 cm and 5 cm.

It is remarkable that the means 20 for adjusting the retaining distance can comprise both discrete adjustment elements used to make approximate adjustments to the overall length of the harnesses according to the patient's anatomy, and continuous adjustment elements used to make fine adjustments to the suspension stress F.

Moreover, according to a preferential embodiment, the retaining means 2 contains a framing element 30 connected to the slings 6, 7, as shown in FIG. 5.

Advantageously, such a framing element 30 can be used to reinforce the sub-urethral support and to determine one or several specific points of compression.

More specifically, the framing element 30 is preferably formed by a cross piece 31, whose center is substantially in register with the center line (L) which divides the support element 3 into its left area and its right area, and whose branches 32, 33, 34, 35 are each connected to the extremity of a harness 10, 11.

In a particularly preferential manner, the framing element and one and/or the other of the harnesses 10, 11 consist of a single piece.

Thus, as shown in FIG. 5, the branches 32, 33, 34, 35 of the cross piece can advantageously form the captive extremities of the strands 10A, 10B, 11A, 11B; i.e., the cross piece 31 is formed by the sub-urethral crossing of the left and right strands 10, 11.

Preferably, the support element 3 is formed, at least partially and preferably totally, by a flexible plate 40.

The said flexible plate 40 can, for example, consists in a fabric, notably knitted, or non-woven, based on a colonizable material such as polypropylene, in order to guarantee integration of the said flexible plate with the supported organ, in this case the urethra U and/or the bulbospongious muscle, and to avoid any risk of relative sliding of said organ with respect to said flexible plate 40.

The said flexible plate 40 is also preferably able to substantially change shape into a "U" form, as shown in FIGS. 3 and 4, in order to partially envelop the urethra U and/or, as appropriate, the whole formed by the urethra U, the cavernous body CC and the bulbospongious muscle MBC.

The flexible plate 40 forms therefore preferably both the support element 3 and the lateral holding elements 12, 13.

Thus, the retaining means 2 can advantageously marry the inferior and lateral portions of the urethra U and/or the bulbospongious muscle, so as to firstly, spread the suspension stress F over a significant tissue surface area and secondly, limit the displacement of the urethra U with respect to the prosthesis 1 and the symphysis pubica SP.

Thus, a particularly stable and atraumatic suspension is advantageously obtained.

Preferably, the framing element 30 is flexible and connected to the flexible plate 40.

Thus, the retaining means can have a multi-layer structure, in which the framing elements 30 are opposite the support element 3.

In particular, the cross piece 31 can be subjected to the flexible plate 40 by gluing or stitching.

Moreover, the said cross piece 31 will be preferably arranged so that the harnesses emerge substantially at the corners of the retaining means 2 and more precisely of the flexible plate 40.

It is remarkable that the presence of framing means 30 makes it possible to advantageously first, define in space, a relatively rigid preferential compression point, under the support element 3, substantially at the crossing of harnesses, and secondly, avoid the puckering of the flexible plate 40, all of which facilitates the placing of the prosthesis and makes the retaining means 2 resistant in time.

Naturally, the framing element 30 is not at all limited to a particular shape, and could comprise a reinforcing edge along, for example, substantially the contours of the flexible plate 40.

Moreover, the flexible area 40 comprises preferably one or more stitching areas 41 intended to be stitched to the bulbospongious muscle MBC in order to immobilize said bulbospongious muscle within the retaining means 2. Preferably, as shown in FIG. 5, the stitching area 41 will substantially extend to the edge of the flexible plate 40.

According to a preferential embodiment, the depth D1 of the support element 3, and more generally the flexible plate 40; i.e., its (overall) dimension considered along the main extension direction XX' of the urethra U and "flat", i.e., when prosthesis 1 is resting opened out on a flat surface, is greater than, or equal to its width D2, i.e., to its (overall) dimension considered along a transversal lateral direction YY' to the said main extension direction XX' of the urethra in the same conditions.

For example, the depth D1 can be substantially included between 40 mm and 60 mm, and the width D2 between 30 mm and 50 mm.

Thus, the suspension means 2 advantageously has the form of the hammock, or a sort of cradle marrying the anatomical form of the urethra and/or of the bulbospongious muscle, and capable of distributing the suspension stress F over a significant length of the latter.

Moreover, in order to adapt as best as possible to the patient's anatomy, the support element 3, and more generally the flexible plate 40 is preferably substantially quadrangular, and particularly preferably substantially trapezoidal; i.e., the width of its anterior edge 3A is substantially less than or equal to the width of its posterior edge 3P.

Moreover, the prosthesis 1 of the invention can comprise an inflatable means of compression 50 which is put down at the level of the support phase 3, between the retaining means 2 and the urethra U, and which is arranged in a manner to be able to, when inflated, exert, as shown in FIG. 4, a compression of the urethra against the tissues above the latter, for example the transversal ligament of the pelvis.

Thus, advantageously, the prosthesis 1 of the invention can combine a separate suspension stress F and compression stress P, said compression stress P being able to reduce the urethral lumen in order to perform a blocking function compensating a sphincterian deficiency. The prosthesis 1 of the invention can therefore be considered an alternative, advantageously simple and inexpensive, to artificial sphincters of the prior art.

More precisely, the inflatable means of compression 50 is advantageously supported on the bottom part of the retaining means 2 to exert an additional pressure P on the urethra which tends to push the bottom wall of the latter towards the symphysis pubica.

Preferably, the inflatable means of compression 50 comprises a cushion 51 which is arranged substantially in register with the center line dividing the support element surface 3 substantially parallel to the main extension direction XX' of the urethra U, as illustrated in FIG. 4.

The said cushion can notably be lodged in a "kangaroo" pouch, arranged under the surface of the support element 3 by a fold in the flexible plate 40.

It is remarkable that this embodiment includes preferably a cross piece 31, as described above, so as to give the cushion 51 a particularly solid point of support on the retaining means 2. Thus, the compression stress P will preferably act in a localized and differential manner with respect to the overall suspension stress F.

In a particularly preferential manner, the inflatable means of compression 50 is connected to a fluid reservoir 54, such as an implantable site, by means of flexible tubing such as a catheter 55.

Preferably, as shown in FIG. 3, the implantable site 54 is arranged to rest, in a stable and rigid manner, against the anterior side of the symphysis pubica SP.

Moreover, the prosthesis 1 can comprise fluid transfer means, such as a remote controlled pump or a pear enabling the patient to control at will by inflating and deflating the cushion 51, and thus permit miction or, on the contrary, guarantee continence.

Moreover, the prosthesis 1 of the invention can be advantageously designed to treat cervico-cystoptosis combined with incontinence in females.

Figures 8B, 9:
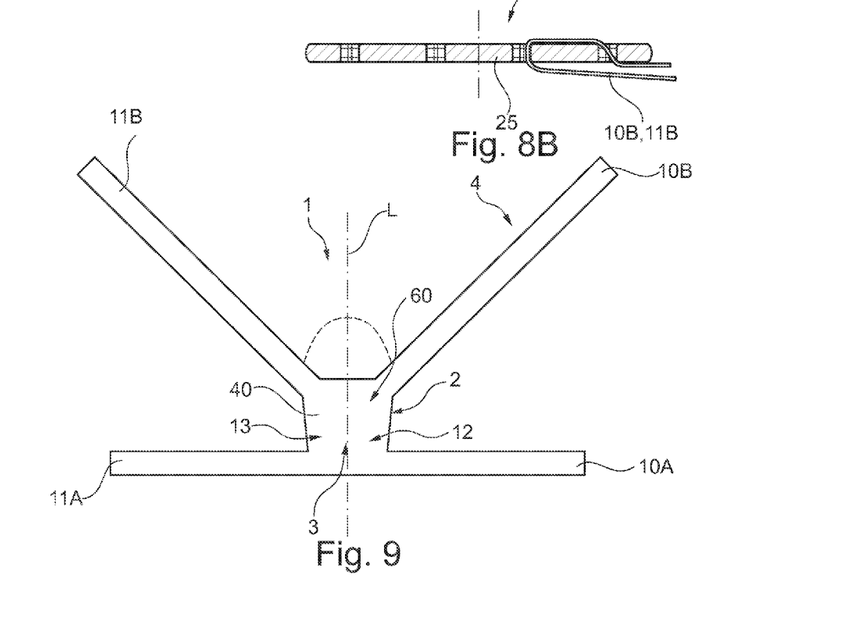
FIG. 9 illustrates, from a schematic top view, an embodiment of the prosthesis, according to the invention, particularly suited to the combined treatment of female incontinence and cervico-cystoptosis.
Figure 11:
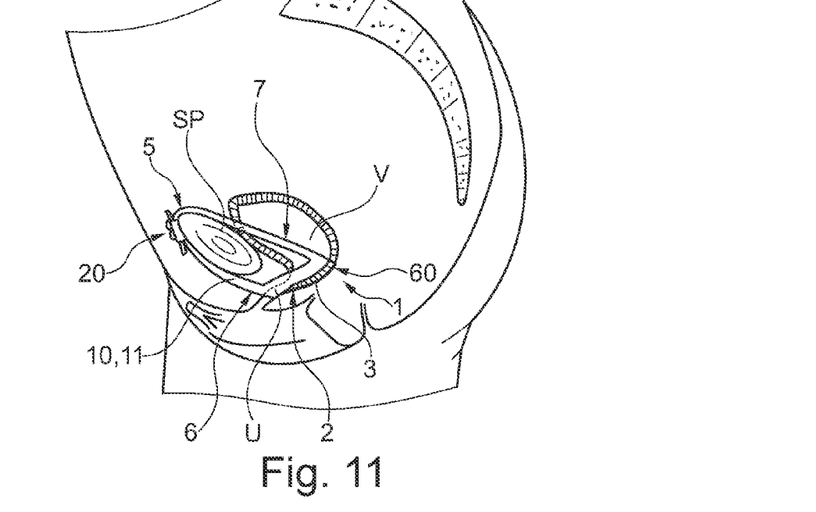
FIG. 11 illustrates, from a simplified side sectional view, the implementation, in a female, of the prosthesis shown in FIG. 9.

To this effect, as shown in FIGS. 9 and 11, the suspension means 2 can have a subvesical extension 60 designed to bear up against the bladder V.

Moreover, it is remarkable that, with this embodiment, the posterior strands 10B, 11B, are preferably oriented obliquely with respect to the edges of the flexible plate, in order to enhance the ergonomic aspect of the prosthesis 1.

Advantageously, the subvesical extension 60 can also extend beyond the points of fixing of the posterior strands to the retaining means, between said posterior strands and, for example, form a flap with a rounded edge, as shown in dotted lines in FIG. 9.

As shown in FIG. 11, the subvesical extension is designed to support at least the base of the latter, whilst the posterior slings 7 are arranged to go around both sides of the bladder V, and connect the said subvesical extension 62 to the bearing element 5.

Thus, the prostheses 1 can support the bladder V by suspending the latter, as well as suspending the urethra, to the symphysis pubica.

Advantageously, a single intervention thus suffices to treat simultaneously a prolapse and incontinence.

Naturally, this invention is not at all limited to a particular embodiment. Thus, the invention can concern solely, independently of the presence of a means for adjusting the retaining distance, an implantable prosthesis intended to treat incontinence comprising a retaining means having a support element designed to be placed under the urethra, in order to prevent the latter moving away in the direction of the lower pelvis, and to prevent uncontrolled intraurethral flow, said prosthesis provided with a symphyseal suspension means designed to suspend the said retaining means to the symphysis pubica, and to hold the support element at a substantially constant distance from the said symphysis pubica, called the retaining distance.

Moreover, this invention relates to an ancillary designed to facilitate the placement of the above-described prosthesis, and more particularly to facilitate the passage of posterior slings 7 into the retropubic space whilst ensuring that the integrity of the bladder is respected.

Figure 13:
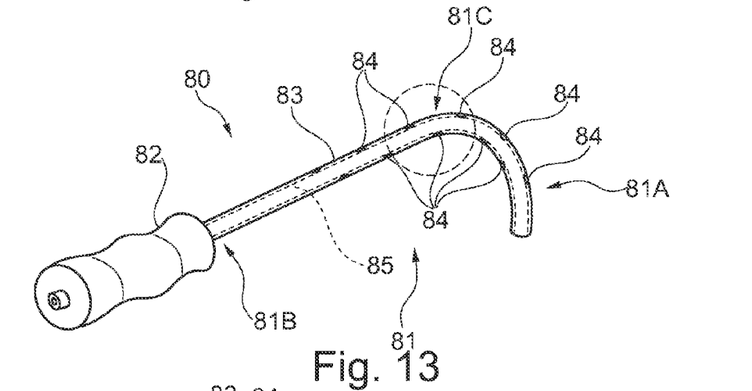
FIG. 13 illustrates, from a general perspective view, an embodiment of the surgical instrument of the invention.
Figure 14:
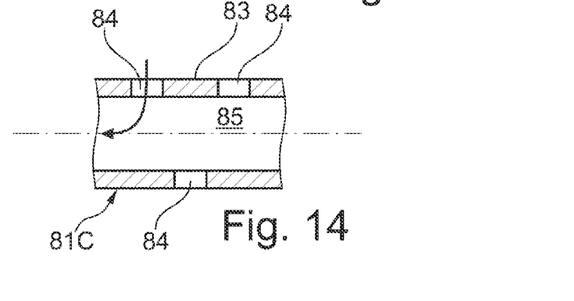
FIG. 14 illustrates, from a partial longitudinal sectional view, a part of the surgical instrument of FIG. 13.

As shown in FIGS. 13 and 14, the ancillary of the invention takes the form of a surgical instrument 80 provided with an introduction element 81 designed to be pushed into the tissues located in the retropubic space in order to create a passageway therein for one or the other of the slings 6, 7.

The said introduction element 81 comprises at least a proximal portion 81A arranged to penetrate the tissues, a distal portion 81B connected to a gripping means 81, such as a handle and an intermediate section 81C which connects the proximal portion 81A to the distal portion 81B, and has an external lateral surface 83 in contact with the tissues traversed.

An important characteristic of the invention is that the intermediate section 81C comprises at least a lateral orifice 84 connecting its external lateral surface 83 to a collecting duct 85 so as to be able to collect the liquid contained in the bladder when the introduction element accidentally perforates the latter.

Thus, a flow of urinary liquid or of colored liquid preliminary injected into the bladder immediately informs the surgeon that the introduction element 81 is traversing the bladder draining its content; i.e., that the said bladder has been accidentally perforated and that it is therefore necessary to intervene to restore its operation.

Naturally, the introduction element 81 is sufficiently rigid to create a passageway in the tissues, and to route its way through the tissues when the surgeon exerts a pushing force on the gripping element 82.

To this effect, the extremity of the proximal portion 81C can be provided with a penetration device, for example, a tip, which may be blunt and/or removable, and is preferably made from a polymer material.

Moreover, the introduction element will be preferably curved to form a type of hook, thereby facilitating the creation of a peri-symphyseal passageway, without taking the risk of perforating deeper anatomical regions.

Moreover, the introduction element 81 will preferably be long enough that its' proximal portion 81A can reemerge outside of the tissues, under the pubis, whilst its distal portion 81B with the gripping means 82 is still emerging from suprapubic tissues.

With a preferred embodiment, the introduction element is formed from a curved, hollow rod, metallic for example, having preferably a cylindrical geometry with a circular base, the collecting duct 85 running inside the said rod and emerging in free air, or in a pocket provided for this purpose at the distal extremity 81B Preferably, the instrument 80 has several lateral orifices 84 drilled substantially radially in the thickness of the rod's wall and arranged along the introduction element.

With a preferred embodiment, the lateral orifices 84 are arranged in several points along the circumference of the introduction element so as to be able to drain the bladder liquid regardless of the orientation of the said introduction element 81.

The said introduction element 81 is therefore preferably multi-perforated, both along its length and around its edge.

Even though the ancillary of the invention is particularly suited to the implementation of a prosthesis 1 as described above, its usage is in no way thereto limited. Thus, it is entirely conceivable to use, for other purposes, a surgical instrument with an introduction element provided with one or more lateral orifices 84 connecting its external lateral surface 83 to a collecting duct 85 so as to be able to collect the liquid contained when said introduction element accidentally perforates an organ.

Naturally, the invention also concerns a surgical kit containing a prosthesis to treat incontinence 1 according to the invention, and a surgical instrument 80 as described above.

This invention also relates to a surgical method to treat incontinence per se.

Such a method will now be briefly described, with reference to the implantation of a prosthesis 1 according to the invention using a surgical instrument 80 according to the invention.

More particularly, the described method refers to a peri-symphyseal suspension, whereby it is understood that a substantially similar method can be applied to obtain a peri-osseous suspension to the ischiopubic or iliopubic branches by trans-obturator route.

According to the invention, the said surgical method comprises an engagement step (a) during which is engaged, under the urethra U a retaining means 2 with a support element 3 designed to prevent the urethra moving away in the direction of the lower pelvis, and to prevent any uncontrolled intra-urethral flow.

With males, the said retaining means 2 will preferably be placed under the bulbospongious muscle MBC, in contact against the latter, whilst with females, the support element 3 of the retaining means 2 will be preferably placed in contact against the urethra itself.

According to an important characteristic of the invention, the said surgical method also comprises an atraumatic bone suspension step (b) during which the retaining means is suspended to the pubic bone OP, using an atraumatic suspension means 4 so that the support element 3 be kept at a distance substantially constant from the pubic bone OP, and more particularly from the symphysis pubica SP, called the retaining distance $d_0$.

Preferably, the suspension step (b) constitutes a suspension step to the symphysis pubica SP.

Thus, the urethra U is "imprisoned" or tightly fitted inside a space delimited by firstly, the symphysis pubica SP, and secondly, the support element 3 located at a distance $d_0$.

In this respect, it is remarkable that a surgical method including the engagement step (a) and then a symphyseal suspension step (b'), atraumatic or invasive, can constitute an invention per se.

In a particularly preferential manner, the atraumatic suspension step (b) comprises a peri-osseous penetration sub-step (b1), and more particularly, a peri-symphyseal penetration sub-step, during which a bearing element 5 is placed astride a portion of the pubic bone, and more particularly on the symphysis pubica SP, and the retaining means 2 is connected to said bearing element 5 using at least one anterior sling 6 passing in front of the pubic bone, respectively the symphysis pubica SP, and at least a posterior sling 7 passing behind the said pubic bone, respectively the said symphysis pubica SP in the retropubic space.

Access to the concerned anatomical region depends notably on the patient's sex.

With male patients, the surgeon preferably performs a transversal, horizontal peno-scrotal incision which permits, following longitudinal incision of the superficial planes (subcutaneous cellular tissue and superficial fascia of urogenital diaphragm) to expose the inferior and lateral faces of the urethra and of the bulbospongious muscle.

The surgeon then introduces his index finger in the angle located between the inside of the bulbourethral muscle on the inside and the branch of the cavernous body on the outside, so as to locate the bottom edge of the ischiopubic branch and initiate the (ascending) passageway.

The surgeon then carries out a transversal suprapubic incision of 2 to 3 cm, at two finger thicknesses from the middle line up to the sheath of the rectus abdominis muscle, which is also incised. The surgeon then inserts his second index in the incision to create, from top to bottom, a passageway at the level of the posterior face of the pubis up to the pelvic floor and operates the junction with the index already introduced from bottom to top by the peno-scrotal incision.

A suitable ancillary passed from top to bottom through the passageway so formed is used to take hold of the posterior strand, and to exteriorize said strand via the suprapubic incision.

Advantageously, the surgeon can use a surgical instrument 80 to create the passageway ("tunnel drilling" operation) and then take hold of the posterior strand.

To this end, he introduces, using force, the introduction element 81 via the suprapubic incision, and pushes it in progressively wrapping its curved part around the symphysis pubica, until the proximal extremity reemerges to free air.

Preferably, the drilling step using an instrument according to the invention is preceded by a step wherein the bladder is filled with colored liquid in order to facilitate the detection of a possible complication.

In the event of abnormal flow through the collecting duct 85 during this operation, the surgeon carries out a fibroscopy check to diagnose the nature and scale of the bladder perforation in order to undertake remedial action.

The same maneuver is repeated on the opposite side (on the right side if the first maneuver took place on the left) to put the second posterior strand in place.

A gripping ancillary is then introduced via the same suprapubic incision, and then passed in front of the pubis to reach the latero-urethral space and take hold of the anterior strand to lift up the latter and exteriorize it via the said suprapubic incision.

With female patients, the exposure of the urethra is preferably obtained using a vertical incision of the anterior vagina wall. The surgical gesture enabling the passage of the strands making up the harnesses is done in a substantially similar manner to that which has been described for male patients.

The surgical methods of the invention also comprises a suspension tension adjustment step (c) during which the medical practitioner adjusts in vivo the retaining distance $d_0$ in order to adjust the suspension stress F exerted by the support element 3 on the urethra U.

More precisely, the said suspension tension adjustment step (c) can consist in a sub-step (c1) for adjusting the length of the slings during which the length of one or the other of the slings 6, 7, and more precisely, of the harnesses, 10, 11 is adjusted.

To this end, the surgeon can join the anterior strand 10A and the corresponding posterior strand 10B using a tightening loop 26 in order to re-create the corresponding harness 10, and then adjust the length of the said "sliding" harness by pulling on the free extremity of one of the strands 10A, 10B passed through the said tightening loop 26.

In particular, the surgeon can select an initial length of the harness, and then proceed in an iterative manner, by a succession of lengthening and/or shortening operations, to select the most appropriate length given the suspension stress to be obtained.

With males, the surgical method of the invention can also include a stabilization step (d) during which the bulbospongious muscle MBC is stitched to the retaining means 2, and more precisely to the flexible plate 40. The said stabilization step (d) preferably takes place prior to the suspension tension adjustment step (c) and more precisely, prior to creation of the harnesses by assembling their respective strands.

With females, the surgical methods of the invention can include a vesical suspension step (e) during which a sub-vesical extension 60 is introduced to the retaining means 2 under the bladder V in order to jointly support the urethra and the said bladder.

More particularly, the said subvesical suspension step (e) can include a sub-step (e1) during which the proximal extremity of the subvesical extension 60 is connected to the bearing element 5 by means of a posterior sling 7, by passing the two posterior strands 10B, 11B, one to either side, around each side of the bladder.

Naturally, the placement of such a subvesical extension requires a more sophisticated subvesical dissection than that described above. The adjustment of the suspension tension F remains advantageously identical to that described above.

Thus, the prosthesis of the invention can be used advantageously to efficiently treat practically all cases of urinary incontinence for a moderate cost, and without causing significant traumatism for the patient.

Moreover, the differential action exerted firstly by the suspension means, and secondly by the inflatable compression means make it possible to easily adapt said prosthesis to the severity of the incontinence to treat.

Lastly, the stability and atraumatic character of the said prosthesis 1 considerably reduce the probability of having to repeat a medical intervention, by minimizing tissue erosion, both as regards the urethra as well as regards the support points used to suspend the prosthesis.

POSSIBILITY OF INDUSTRIAL APPLICATION

The invention finds its industrial application in the designing and manufacturing of prostheses to treat incontinence.

The invention claimed is:

1. An implantable prosthesis for the treatment of incontinence of a patient, comprising a retaining device having a support element designed to be placed under a urethra, directly against said urethra for females and against a bulbospongious muscle for males, in order to prevent the urethra from moving away in a direction of a lower pelvis, and to prevent any uncontrolled intra-urethral flow, said support element having a top face designed for facing the urethra when implanted and a bottom face opposed to said top face, said implantable prosthesis further comprising:
   an atraumatic suspension device comprising at least a first suspension harness and a second suspension harness, said first suspension harness comprising a first anterior sling adapted to pass in front of the pubic bone, a first bearing element, and a first posterior sling adapted to pass behind the pubic bone, said second suspension harness comprising a second anterior sling adapted to pass in front of the pubic bone, a second bearing element, and a second posterior sling adapted to pass behind the pubic bone, said first and second suspension harnesses being configured to hold the support element at a substantially constant retaining distance from the pubic bone, and said atraumatic suspension device being a suspension device designed so as not to damage tissues on which it is designed to rest and so as to respect the integrity of the pubic bone, and
   an adjusting device for reversibly adjusting the retaining distance according to the patient's anatomy,
   wherein said first suspension harness is divided into a first strand forming the first anterior sling and a second strand forming the first posterior sling,
   wherein said second suspension harness is divided into a first strand forming the second anterior sling and a second strand forming the second posterior sling,
   wherein each of the first and second strands of the first suspension harness and the first and second strands of the second suspension harness have a captive extremity, attached to the retaining device, and a free extremity, the first and second strands of the first suspension harness and the first and second strands of the second suspension harness being designed to be joined together, so as to form, in cooperation with a part of the retaining device, a loop overlapping part of the pubic bone and resting on said pubic bone, and
   wherein said implantable prosthesis further comprises a framing element formed by a cross-piece, the cross-piece being formed by a crossing of the first and second strands of each of the first and second suspension harnesses, and wherein said framing element is arranged on the bottom face of the support element to reinforce the support element and determine at least one point of compression.

2. The implantable prosthesis according to claim 1, wherein said adjusting device is configured to allow continuous modification of the retaining distance.

3. The implantable prosthesis according to claim 1, wherein said adjusting device has an adjusting element to adjust a length of at least one of said slings, said adjusting element comprising a tightening loop wrapped around said at least one of said slings and arranged to enable continuous adjustment of the length of said at least one of said slings.

4. The implantable prosthesis according to claim 1, wherein said suspension device comprises a peri-symphyseal suspension device configured to suspend the retaining device to a symphysis pubica.

5. The implantable prosthesis according to claim 1, wherein said implantable prosthesis further comprises an inflatable device of compression positioned at a level of the support element such that the inflatable device of compression is configured to be positioned between the retaining device and the urethra, and fitted in such a way that, when inflated, it exerts a compression on the urethra against the tissues above the latter.

6. The implantable prosthesis according to claim 5, wherein the support element is formed by a flexible plate, the inflatable device of compression comprises a cushion, and the flexible plate has a fold forming a kangaroo pouch in which is lodged said cushion.

7. The implantable prosthesis according to claim 6, wherein the implantable prostheses further comprises a fluid transfer device enabling control of inflating and deflating of the cushion.

8. The implantable prosthesis according to claim 5, wherein the inflatable device of compression is connected to a fluid reservoir by means of flexible tubing.

9. The implantable prosthesis according to claim 1, wherein said retaining device has a subvesical extension designed to bear up against a bladder.

10. The implantable prosthesis according to claim 1, wherein the atraumatic suspension device is flexible and has low extendability.

11. The implantable prosthesis according to claim 1, wherein each of the first and second suspension harnesses is non-adhesive.

12. The implantable prosthesis according to claim 1, wherein at least one of the first and second suspension harnesses is formed on a basis of a band made from a polymer.

13. The implantable prosthesis according to claim 1, wherein the support element is formed by a flexible plate being substantially quadrangular, and at least one of the first and the second suspension harnesses emerges substantially at corners of the flexible plate.

14. The implantable prosthesis according to claim 1, wherein the support element is formed at least partially by a flexible plate, and wherein the implantable prosthesis comprises a multilayer structure in which the framing element is opposite to the support element, and wherein the framing element is flexible and connected to the flexible plate.

15. The implantable prosthesis according to claim 1, wherein each of the first anterior and first posterior slings, and each of the second anterior and second posterior slings, are flat bands having a width between 0.5 centimeters and 3 centimeters.

16. A surgical method for treating incontinence, said surgical method comprising:
an engagement step comprising an engagement, under a urethra, directly against said urethra for females and against a bulbospongious muscle for males, of a retaining device of an implantable prosthesis, said retaining device comprising a support element configured to prevent the urethra from moving away in a direction of a lower pelvis, and to prevent any uncontrolled intra-urethral flow, and
an atraumatic bone suspension step comprising the suspension of the retaining device to a pubic bone, by using an atraumatic suspension device so that the support element may be kept at a distance substantially constant from the pubic bone called a retaining distance, and wherein said atraumatic suspension device is designed so as not to damage tissues on which it is designed to rest and so as to respect the integrity of the pubic bone, and wherein the atraumatic bone suspension step comprises a peri-osseous penetration sub-step during which a bearing element is placed astride a portion of the pubic bone and the retaining device is connected to said bearing element using at least a first suspension harness and a second suspension harness, said first suspension harness comprising a first anterior sling adapted to pass in front of the pubic bone, a first bearing element, and a first posterior sling adapted to pass behind the pubic bone in a retropubic space, said second suspension harness comprising a second anterior sling adapted to pass in front of the pubic bone, a second bearing element, and a second posterior sling adapted to pass behind the pubic bone in the retropubic space,
wherein said first suspension harness is divided into a first strand forming the first anterior sling and a second strand forming the first posterior sling,
wherein said second suspension harness is divided into a first strand forming the second anterior sling and a second strand forming the second posterior sling, and
wherein each of the first and second strands of the first suspension harness and the first and second strands of the second suspension harness have a captive extremity, attached to the retaining device, and a free extremity, said surgical method further comprising a suspension tension adjustment step during which the first and second strands of each of the first and second suspension harnesses are joined together, so as to form, in cooperation with a part of the retaining device, a loop overlapping part of the pubic bone and resting on said pubic bone,
wherein said implantable prosthesis further comprises a framing element formed by a cross-piece, the cross-piece being formed by a crossing of the first and second strands of each of the first and second suspension harnesses, and wherein said framing element is arranged on a bottom face of the support element to reinforce the support element and determine at least one point of compression.

17. A surgical method according to claim 16, wherein the surgical method further comprises a vesical suspension step during which a subvesical extension is introduced under a bladder so as to jointly support the urethra and said bladder.

* * * * *